(12) United States Patent
Eliyahu-Gross et al.

(10) Patent No.: US 10,184,011 B2
(45) Date of Patent: Jan. 22, 2019

(54) HEMOSTATIC DEVICES WITH IMPROVED PROPERTIES AND METHODS OF MAKING SAME

(71) Applicant: Core Scientific Creations Ltd., Kfar Saba (IL)

(72) Inventors: Shani Eliyahu-Gross, Kfar Saba (IL); Yuval Yaskil, Kfar Saba (IL)

(73) Assignee: Core Scientific Creations Ltd., Kfar Saba (IL)

( * ) Notice: Subject to any disclaimer, the term of this patent is extended or adjusted under 35 U.S.C. 154(b) by 0 days.

(21) Appl. No.: 14/719,701

(22) Filed: May 22, 2015

(65) Prior Publication Data
US 2016/0121019 A1 May 5, 2016

Related U.S. Application Data

(60) Provisional application No. 62/073,810, filed on Oct. 31, 2014.

(51) Int. Cl.
*C08L 1/00* (2006.01)
*A61L 15/28* (2006.01)
*C08B 11/12* (2006.01)

(52) U.S. Cl.
CPC .............. *C08B 11/12* (2013.01); *A61L 15/28* (2013.01); *A61L 2400/04* (2013.01)

(58) Field of Classification Search
None
See application file for complete search history.

(56) References Cited

U.S. PATENT DOCUMENTS

| | | | | |
|---|---|---|---|---|
| 2,639,239 A | * | 5/1953 | Elliott | C08B 11/20 106/172.1 |
| 4,579,943 A | * | 4/1986 | Kamide | A61L 15/28 428/532 |
| 5,780,618 A | | 7/1998 | Banker et al. | |
| 7,262,181 B2 | | 8/2007 | Zhang et al. | |
| 7,279,177 B2 | * | 10/2007 | Looney | A61L 15/28 424/443 |
| 8,709,463 B2 | | 4/2014 | Looney et al. | |
| 2002/0010150 A1 | * | 1/2002 | Cortese | A61K 31/715 514/54 |
| 2006/0014721 A1 | * | 1/2006 | Zhang | A61L 15/28 514/57 |
| 2007/0167971 A1 | | 7/2007 | Huey et al. | |
| 2013/0040911 A1 | * | 2/2013 | Soe | A61L 31/048 514/57 |

FOREIGN PATENT DOCUMENTS

| | | | | |
|---|---|---|---|---|
| CN | 101491688 B | 12/2012 | | |
| CN | 101623512 B | 11/2013 | | |
| EP | 0468114 A2 | * 1/1992 | ............. | A61L 15/28 |

OTHER PUBLICATIONS

Kulikowska, Biomedical Engineering, Carboxymethyl Cellulose Oxidation to Form Aldehyde Groups, 2013.*
Ciolacu, Cellulose Chem. Technol. 45 (1-2), 13-21 (2011).*
Celox, "How Celox Works", http://www.celoxmedical.com/usa/usaresources/resourceshow-it-works/, Retrieved from the Internet Sep. 8, 2015, pp. 1-5.
R. F. Bellamy, "The causes of death in conventional land warfare-implications for combat casualty care research", Mil. Med., 149 ,1984, pp. 55-62.
F. K. Butler et al., "Battle field trauma care then an now: a decade of Tactical Combat Casualty Care" J. Trauma Acute Care Surg. 73(Suppl5), 2012, pp. 395-402.
P. Calvini et al., "Viscometric determination of dialdehyde content in periodate oxycellulose Part I" Methodology. Cellulose, 11, 1, 2004, pp. 99-107.
P. Calvini et al., "Viscometric determination of dialdehyde content in periodate oxycellulose Part II" Topochemistry of oxidation. Cellulose, 13, 5, 2006, pp. 571-579.
H. R. Champion et al., "A profile of combat injury", J. Trauma, 54 (Suppl), 2003, pp. 13-19.
V. B. Chavan et al., "Morphology of cellulose and oxidised cellulose in powder form." Carbohydrate polymers, 50, 1, 2002, pp. 41-45.
B. Drew et al., "Application of Current Hemorrhage Control Techniques for Backcountry Care: Part One, Tourniquets and Hemorrhage Control Adjuncts." Wilderness & environmental medicine, 26,2, 2015, pp. 236-245.
J. Granville-Chapman et al., "Pre-hospital haemostatic dressings: a systematic review" Injury.;42, 2011, pp. 447-459.
A. R. Khare et al., "Measurement of the swelling force in ionic polymer networks: I. Effect of pH and ionic content", J. Control. Release 22, 1992, pp. 239-244.

(Continued)

*Primary Examiner* — Layla D Berry
(74) *Attorney, Agent, or Firm* — Potomac Law Group, PLLC; Jeremy A. Cubert, Esq.

(57) ABSTRACT

Hemostatic devices and methods of making same are disclosed. Disclosed hemostatic devices include biocompatible non-oxidized regenerated cellulose. The disclosed hemostatic devices are effective in providing and maintaining hemostasis in cases of moderate to severe bleeding caused by non-compressional and/or non-tourniquetable injuries, among other things. The disclosed methods enable manufacture of a bioabsorbable, biocompatible, biodegradable carboxylmethyl cellulose having high stability and high adherence.

4 Claims, 2 Drawing Sheets

(56) References Cited

OTHER PUBLICATIONS

B. S. Kheirabadi et al., "Development of a Standard Swine Hemorrhage Model for Efficacy Assessment of Topical Hemostatic Agents" The journal of TRAUMA Injury infection and Critical Care, 71, 1(Supplement), 2011, pp. 139-146.
J. F. Kragh et al., "Practical use of emergency tourniquets to stop bleeding in major limb trauma" J. Trauma. 64 (Suppl), 2008, pp. 38-50.
J. F. Kragh et al., "Minor morbidity with emergency tourniquet use to stop bleeding in severe limb trauma: research, history, and reconciling advocates and abolitionists" Mil Med., 76, 2011, pp. 817-823.
L. Littlejohn et al., "Application of Current Hemorrhage Control Techniques for Backcountry Care: Part Two, Hemostatic Dressings and Other Adjuncts" Wilderness & environmental medicine, 26,2, 2015, pp. 246-254.
A. E. Pusateri, "US Department of Defense Hemorrhage and Resuscitation Research and Development Program" RDCR Conference, Bergen, Norway, 2012, pp. 1-47.
M. Silberberg-Bouhnik et al., "Osmotic deswelling of weakly charged poly(acrylic acid) solutions and gels", J. Polym. Sci. 33, 1995, pp. 2269-2279.
J. D. Smart, "The basics and underlying mechanisms of mucoadhesion" Advanced Drug Delivery Reviews 57, 2005, pp. 1556-1568.
A. J. Varma et al., "A study of crystallinity changes in oxidised celluloses" Polymer Degradation and Stability, 49,2, 1995, pp. 245-250.
E. C. Yackel et al., "The Oxidation of Cellulose by Nitrogen Dioxide" Journal of the American Chemical Society, 64,1, 1942, pp. 121-127.
C. Zhu et al., "Effect of Fabric Structure and Yarn on Capillary Liquid Flow within Fabrics" Journal of Fiber Bioengineering and Informatics 6, 2, 2013, pp. 205-215.
H. D. Heydarzadeh et al., "Catalyst-Free Conversion of Alkali Cellulose to Fine Carboxymethyl Cellulose at Mild Conditions", World Applied Sciences Journal, vol. 6, No. 4, 2009, pp. 564-569.
PCT International Search Report and Written Opinion dated Jan. 25, 2016, International Application No. PCT/IB2015/058369, pp. 1-13.
Frank D. Butler, "Tactical Combat Casualty Care: Updated 2009", The Journal of TRAUMA: Injury, Infection, and Critical Care, vol. 69, No. 1, Jul. 2010, pp. S10-S13.
R. L. Stillwill et al., article "Oxidized Cellulose", excerpt from "Handbook of Biodegradable Polymers", 1997, pp. 500-501.
Col. John F. Kragh, Jr. et al., "Survival With Emergency Tourniquet Use to Stop Bleeding in Major Limb Trauma", Annals of Surgery, vol. 249, No. 1, Jan. 2009, pp. 1-7.
Antje Potthast et al., "On the nature of carbonyl groups in cellulosic pulps", Cellulose, vol. 12, 2005, pp. 43-50.
Angela Sauaia, MD. et al, "Epidemiology of Trauma Deaths: A Reassessment", Th Journal of TRAUMA: Injury, Infection, and Critical Care, vol. 38, Issue 2, 1995, pp. 185-193.
John D. Smart, "The Role of Water Movement and Polymer Hydration in Mucoadhesion", Drugs and the pharmaceutical sciences 98, 1999, pp. 11-23.
Agnes Timar-Balazsy et al., "Cellulose Fibres", Chemical Principles of Textile Conversation, 1998, pp. 29-30.
Yuping Zhu et al., "Acyclic forms of [1-13C] aldohexoses in aqueous solution: quantitation by 13C NMR and deuterium isotope effects on tautomeric equilibria" Journal of Organic Chemistry, vol. 66, Issue 19, 2001, pp. 6244-6251.
Detailed Feasibility Analysis of Gauze, Bandages and Absorbent Cotton, Part III, For Department of Industries Ministry of Economic Affairs Royal Government of Bhutan by Idrg Consultancy Services in Association with Sherpa Consultancy, Feb. 2009, pp. 1-67, (available from http://www.moea.gov.bt/documents/files/pub9pd8630bc.pdf).
Fred B. Kilmer, "Standards for Absorbent Cotton and Absorbent Gauze", Scientific Section, San Francisco, The Journal of the American Pharmaceutical Association (1912), vol. 4, Issue 10, 1915, pp. 1228-1232.
"Project Report on Surgical Absorbent Cotton, MSME" Development Institute, Ministry of Micro, Small & Medium Enterprises, Government of India, Dec. 2010, pp. 1-11,(available from http://www.dcmsme.gov.in/reports/surgicalabsorbentcotton.pdf).
Jule Credou et al., "Cellulose: from biocompatible to bioactive material", Journal of materials chemistry B, Royal Society of Chemistry, 2014, 2, pp. 4767-4788.
International Preliminary Report on Patentability issued in International Patent Application No. PCT/IB2015/058369 dated May 2, 2017.
International Search Report issued in International Patent Application No. PCT/IB2015/058369 dated Jan. 25, 2016.
Written Opinion issued in International Patent Application No. PCT/IB2015/058369 dated Jan. 25, 2016.

* cited by examiner

HEMOSTATIC DEVICES WITH IMPROVED PROPERTIES AND METHODS OF MAKING SAME

CROSS-REFERENCE TO RELATED APPLICATIONS

This application claims priority to and the benefit of U.S. Provisional Application Ser. No. 61/073,810, filed Oct. 31, 2014, which is hereby incorporated by reference.

BACKGROUND

Field of the Disclosure

The present disclosure relates generally to hemostatic devices, and more particularly, to hemostatic devices based on non-oxidized regenerated cellulose.

Background Information

In the treatment of moderate to severe traumas, controlling bleeding is essential and critical to minimize blood loss. The process of healing injuries begins with the adhesion and agglutination of platelets to injured tissue, and the simultaneous liberation of thromboplastin from injured cells. To aid in this process, hemostatic wound dressings are used for sealing an injured site, thereby reducing the loss of blood, activating the clotting mechanisms and promoting hemostasis.

Conventional hemostatic wound dressings include knitted or non-woven fabrics comprising carboxylic-oxidized cellulose. Typically, oxidized cellulose is implemented as carboxylic-oxidized regenerated cellulose comprising reactive carboxylic acid groups which have been treated to increase the homogeneity of the cellulose fiber.

Due to its biodegradability and its bactericidal and hemostatic properties, oxidized cellulose that has been modified to contain carboxylic acid moieties has long been used as a topical hemostatic wound dressing in a variety of bleeding traumas, such as, wounds, internal organ traumas, and surgical procedures.

While the absorbency of body fluids and the hemostatic action of currently available carboxylic-oxidized cellulose hemostats are adequate for applications where mild to moderate bleeding is encountered, they are not known to be effective for providing and maintaining hemostasis in cases of severe bleeding, and non-compressional or non-tourniquetable wounds. Examples of severe bleeding and non-compressional or non-tourniquetable wounds include arterial puncture, liver resection, blunt liver trauma, blunt spleen trauma, aortic aneurysm, etc., where a relatively high volume of blood is lost at a relatively high rate. In such instances, a higher degree of hemostasis is required and the improved hemostasis needs to be implemented over a shorter period of time. Additionally, there is no clinical data that oxidized carboxymethyl cellulose (CMC) is effective in patients with coagulopathies.

SUMMARY

The present disclosure is not meant to be limited by the following summary. The summary is meant to provide a concise and convenient description of the nature and subject of the described embodiments and implementations, without restricting or limiting any of the described embodiments and implementations or other descriptions in this disclosure.

The present disclosure describes devices with improved hemostatic properties. Additionally, the disclosure provides improved methods for manufacturing such devices.

In an embodiment, there is a hemostatic device. The hemostatic device includes a cellulose derivative composition comprising at least one polymer and at least one counter ion, the cellulose derivative composition configured to interact with blood through a hydration process wherein the polymer interacts with a water component of the blood upon dissociation of the at least one counter ion.

In another embodiment, there is a method for preparing a hemostatic composition. The method includes reacting a non-oxidized cellulose with an alkalization agent in the presence of at least one solvent to form an alkali-cellulose, and reacting the alkali-cellulose with at least one of a monohaloacetic acid or a salt thereof to form a cellulose derivative.

In some embodiments, improved hemostatic devices provide and maintain effective hemostasis when applied to wounds or traumas. In these embodiments, improved hemostatic devices are effective in providing and maintaining hemostasis in several cases including moderate to severe bleeding.

In other embodiments, improved hemostatic devices provide a unique level of adherence and gel stability, even in massive bleeding scenarios. In such scenarios, improved hemostatic devices allow high efficiency bleeding control in non-compressional and/or non-tourniquetable injuries such as vascular breaches, heart traumas, lungs injuries, spleen trauma, uterus trauma, placenta trauma, head trauma, spine, skeleton, pelvis wounds, blast wounds, fracture wounds, transections, amputations, oral and maxillofacial traumas, and the like. In these embodiments, the improved hemostatic devices form a mechanical plug by adhering to a wound cavity and thereby slowing down the blood flow from the wound cavity.

In still other embodiments, improved hemostatic devices have high levels of absorption, thereby intensifying the natural amount of platelets in the plug.

In some embodiments, improved hemostatic devices form a hemodynamic gel when in contact with blood. In these embodiments, the hemodynamic gel absorbs significant amounts of blood and allows natural dynamic coagulation to occur in a contained and focused area.

In some embodiments, polymers used to manufacture the improved hemostatic devices are biocompatible, biodegradable, water-soluble, water-swellable, and the like.

In other embodiments, polysaccharides polymers are used in manufacturing improved hemostatic devices. Examples of polysaccharides are: cellulose, alkyl cellulose (e.g., methylcellulose, alkylhydroxyalkyl cellulose, hydroxyalkyl cellulose, cellulose sulfate, salts of carboxymethyl cellulose, carboxymethyl cellulose, carboxyethyl cellulose, carboxymethyl chitin), hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylose, amylopectin, poly-N-glucosamine, polymannuronic acid, polyglucuronic acid, derivatives, combinations or co-polymers or block co-polymers of any of the above.

In some embodiments, non-oxidized cellulose is used to manufacture the improved hemostatic devices. In these embodiments, the non-oxidized cellulose is amorphous, crystalline or a combination thereof. In an example, the non-oxidized cellulose is a non-oxidized regenerated cellulose.

In other embodiments, improved hemostatic devices are made by chemical modification of non-oxidized regenerated cellulose to form the cellulose derivative sodium carboxymethyl cellulose (Na-CMC), which belongs to the polyelectrolytes polymer family.

In some embodiments, improved hemostatic devices are implemented as sterile gauzes intended for packing into a bleeding wound, to aid in achieving hemostasis. In these embodiments, the gauze is a single-use product made of chemically treated non-oxidized regenerated cellulose. In other embodiments, improved hemeostatic devices are used in combination with other bandages, such as gauze bandages, triangular bandages, tube bandages, pressure bandages, and the like.

In other embodiments, improved hemostatic devices are produced in a carrier form that may be at least one of sponges, flakes, powder, gels, films or foam. In other embodiments, improved hemostatic devices in a carrier form of films and sponges can be produced by completely dissolving the prepared cellulose derivative using a dissolving agent, molding the dissolved cellulose derivative into the desired shape (e.g., for films as thin layers, for sponges with air bubbling), and then evaporating the dissolving agent. Suitable dissolving agents include organic solvents, water, or a mixture of organic solvents.

The present disclosure further relates to a method of manufacturing an improved hemostatic device. The method of manufacturing comprises the following steps: an alkali treatment, an acid solution preparation, a dissolution process, an etherification process, washing and neutralization, drying, and sterilization, among others.

BRIEF DESCRIPTION OF THE FIGURES

The present disclosure can be better understood by referring to the following figures. The components in the figures are not necessarily to scale, emphasis instead being place upon illustrating the principles of the disclosure. In the figures, reference numerals designate corresponding parts throughout the different views.

DETAILED DESCRIPTION

Figure 1:
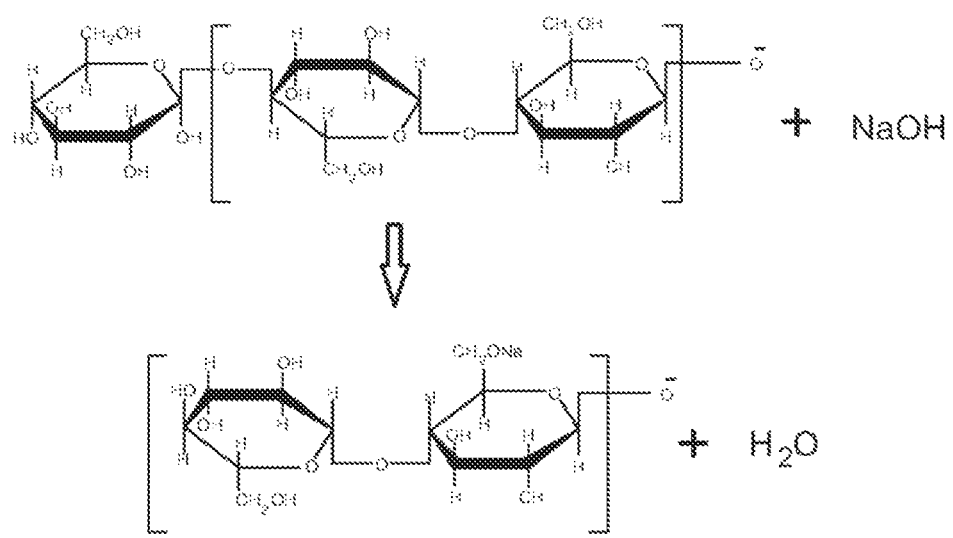
FIG. 1 is a reaction mechanism diagram of an alkali treatment of a non-oxidized regenerated cellulose of a carrier material, according to an embodiment.

The present disclosure is described in detail with reference to certain embodiments. Other embodiments may be used and/or other changes may be made to the embodiments without departing from the spirit or scope of the present disclosure. The illustrative embodiments described in the detailed description are not meant to be limiting of the subject matter presented herein.

Definitions

As used here, the following terms have the following definitions:

"Alkalization agent" refers to an alkali metal hydroxide or alkaline earth metal hydroxide that is used for activating the non-oxidized regenerated cellulose.

"Effective hemostatis" refers to the ability to control and/or abate capillary, venous, or arteriole bleeding within an effective time, as recognized by those skilled in the art of hemostasis. Further indications of effective hemostasis may be provided by governmental regulatory standards and the like.

"Hemodynamic gel" refers to a gel which can absorb platelets and coagulants and allows them to move and react within the gel while maintaining relative stability, thereby forming a severe bleeding physical barrier.

"Main vessel" refers to a vessel where the non-oxidized regenerated cellulose is placed for the chemical treatment.

"Non-oxidized regenerated cellulose" refers to regenerated cellulose that has not yet undergone modifications by oxidation. The oxidation process can be performed in three places: a) on the hydroxyl groups, (b) on the pyranose ring, or (c) in between the chains (opening the etheric connections and shortening the chain length).

"Non-oxidized carboxymethyl cellulose" refers to non-oxidized regenerated cellulose derivative with a carboxymethyl group ($-CH_2-COOA$) bound to at least one hydroxyl group of the glucopyranose monomers that make up the cellulose backbone. A is hydrogen or a mono-, or di-, or tri-valent cation, such as, $Na^+$, $K^+$, $Ag^+$, $Ca^{+2}$, $Al^{+3}$, and the like.

"Regenerated cellulose" refers to cellulose that has been prepared by regeneration (i.e., returned to solid form) from a solution that includes dissolved cellulose fibers.

"Severe bleeding" refers to cases of bleeding where a relatively high volume of blood is lost at a relatively high rate.

"Secondary vessel" refers to a vessel where the reagent solution for the chemical treatment of the non-oxidized regenerated cellulose is prepared.

"Suitable solvent" refers to a solvent where the interactions between polymer segments and solvent molecules are energetically favorable then the polymer-polymer self-interactions. The quality of the solvent depends on both the chemical compositions of the polymer and solvent molecules, and the solution temperature.

DESCRIPTION OF THE DISCLOSURE

The present disclosure provides devices with hemostatic properties that are significantly higher or improved compared to conventional hemostatic devices and also provides methods for manufacturing such devices.

In some embodiments, improved hemostatic devices provide and maintain effective hemostasis when applied to wounds and traumas. In these embodiments, the improved hemostatic devices are effective in providing and maintaining hemostasis in several cases including moderate to severe bleeding, non-compressional and/or non-tourniquetable wounds, and patients with coagulopathies.

In other embodiments, the improved hemostatic devices provide a unique level of adherence and gel stability, even in massive bleeding scenarios. In these embodiments, the improved hemostatic devices provide high efficiency bleeding control for non-compressional, non-tourniquetable injuries such as vascular breaches, heart traumas, lungs injuries, spleen, uterus, placenta, head trauma, spine, skeleton, pelvis wounds, blast wounds, fracture wounds, transections, amputations, oral and maxillofacial wounds, and the like.

In some embodiments, improved hemostatic devices form a mechanical plug by adhering to a wound cavity and thereby slowing down the blood flow from the wound cavity.

In some embodiments, the unique level of adherence is caused by mechanisms created in multiple aspects of the manufacturing process. These mechanisms comprise: swelling of the fabric, contraction, and conductivity, among others.

In some embodiments, the swelling of the fabric allows improved hemostatic devices to absorb large amounts of fluid. These high levels of absorption are due to their stability, which keeps molecular chains unbroken; the initial length of the fibers in the raw materials; and the ionic forces introduced in the manufacturing process.

In other embodiments, improved hemostatic devices possess high levels of absorption, thereby intensifying the natural amount of platelets in the plug by its improved ability to absorb these platelets while allowing them to interact and maintain this state of matter. In some embodiments, the hemodynamic gels form severe bleeding physical barriers. The high levels of blood and water absorbed by the hemodynamic gels allow the resultant high capillary forces between molecular groups to create significant shrinkage within wounds, thereby forming strong adherence and promoting the clotting mechanisms and further adherence through linkage of platelet plugs formed naturally in both wound and gel.

In some embodiments, improved hemostatic devices form hemodynamic gels when in contact with blood. In these embodiments, the hemodynamic gels absorb significant amounts of blood and allow natural dynamic coagulation to occur in a contained and focused area.

In some embodiments, the hemodynamic gel absorbs platelets and coagulants, allowing them to move and react. In these embodiments, the hemodynamic gel keeps the platelets and coagulants contained in the gel and on the wound. Further to these embodiments, a hemodynamic coagulation-promoting gel is created.

In other embodiments, improved hemostatic devices are manufactured with specifically designed molecular functional groups that form new ionic forces between molecules upon break down, thereby causing the chains to swell and drift at a much slower rate, resulting in the creation of hemodynamic gel. The new ionic forces are related to the formation of negatively charged side groups and further occur because the cellulose backbone length is not reduced by oxidation. Therefore, each of the chains contains more ionic charges per chain. Additionally, the new ionic forces maintain the links between the chains for a longer period of time thereby allowing them to keep their integrity until they are isolated and then dissolved.

In some embodiments, polymers used to manufacture the improved hemostatic devices are biocompatible, water-soluble, water-swellable, and the like. In these embodiments, in order to provide the composition with chemical properties suitable for use in hemostatic devices the water-soluble or water-swellable polymers must rapidly absorb blood or other body fluids and form a tacky or sticky gel that adheres to tissue when placed in contact therewith. The fluid-absorbing polymers, when in a dry or concentrated state, interact with body fluid through a hydration process. Once applied to a bleeding site, the polymers interact with the water component in the blood via the hydration process. The hydration three not only provides an adhesive interaction that aids in the hemostatic devices adhering to the bleeding site, but it also serves as a sealant at the bleeding site to stop the blood flow and thus aid in hemostasis provided by the non-oxidized regenerated cellulose.

In some embodiments, polymers used in hemostatic devices are polysaccharides. Examples of polysaccharides are: cellulose, alkyl cellulose (e.g., methylcellulose, alkylhydroxyalkyl cellulose, hydroxyalkyl cellulose, cellulose sulfate, salts of carboxymethyl cellulose, carboxymethyl cellulose, carboxyethyl cellulose, chitin, carboxymethyl chitin), hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylose, amylopectin, poly-N-glucosamine, polymannuronic acid, polyglucuronic acid polyguluronic acid, and derivatives, combinations or co-polymers or block co-polymers of any of the above.

In some embodiments, non-oxidized cellulose is used to prepare the hemostatic devices. In these embodiments, the non-oxidized cellulose is amorphous, crystalline or a combination thereof. In an example, the non-oxidized cellulose is a non-oxidized regenerated cellulose, which has a higher degree of uniformity versus cellulose that has not been regenerated.

In other embodiments, improved hemostatic devices are produced by chemical modification of non-oxidized regenerated cellulose to form the cellulose derivative sodium carboxymethyl cellulose (Na-CMC), which belongs to the polyelectrolytes polymer family.

In some embodiments, when the Na-CMC comes in contact with aqueous fluids, the polymer interacts with water due to the polar ion groups on the side chains resulting in dissociation of the $Na^+$ counter ions, leaving negative carboxyl groups bound covalently to the backbone of the polymer. When this occurs, a negatively charged substance is formed. In these embodiments, the negative polyelectrolyte nature of carboxymethyl cellulose influences the activation of Hageman factor which initiates the contact activation pathway (intrinsic path) of the clotting mechanisms.

In some embodiments, improved hemostatic devices are designed as sterile gauzes intended for packing into a bleeding wound, to aid in achieving hemostasis. In these embodiments, the gauze is a single-use product made of chemically treated non oxidized regenerated cellulose. In other embodiments, improved hemostatic devices are used in combination with other bandages, such as gauze bandages, triangular bandages, tube bandages, and the like.

In still other embodiments, improved hemostatic devices are produced in a variety of carrier forms, such as, for example sponges, powder, flakes, gel, films, foam, among others, for use to control bleeding from a variety of wounds.

Manufacturing Process

The present disclosure is directed to a process of preparing carboxymethyl cellulose comprising the steps of reacting non-oxidized regenerated cellulose with an alkalization agent in the presence of suitable organic solvents, and reacting the alkali-cellulose with monohaloacetic acid or a salt thereof. The monohaloacetic acid can be used as free acid or in its salt form.

In some embodiments, the suitable solvents include water, ethanol, toluene, acetone, 2-propanol, or other suitable organic solvents, or a mixture thereof. In an example, water and ethanol are used as solvents.

In some embodiments, the alkalization agent is sodium hydroxide (NaOH), potassium hydroxide (KOH), calcium hydroxide ($Ca(OH)_2$), or a mixture thereof. In an example, NaOH is used as the alkalization agent. In another embodiment, the monohaloacetic acid is sodium monochloroacetic acid ($ClCH_2COON_a$).

Reaction Description

FIG. 1 is a schematic molecular structure diagram illustrating reaction mechanism 100 of an alkali treatment of a non-oxidized regenerated cellulose of a carrier material, according to an embodiment. In the example of FIG. 1, the non-oxidized regenerated cellulose is in contact with a NaOH solution. In an example, the weight concentration range used in the alkali treatment of non-oxidized regenerated cellulose is from about 0 to about 40% weight/total weight.

In some embodiments, non-oxidized regenerated cellulose is soaked in an 11% w/w NaOH solution (e.g., about 11% $NaOH_{(s)}$), about 21% water, and about 68% ethanol) at about 25° C. until the non-oxidized regenerated cellulose is converted into alkali-cellulose as illustrated in FIG. 1.

During the alkali treatment, the crystalline structure of non-oxidized regenerated cellulose is modified and thus its accessibility to chemicals increases by swelling. The change of crystallinity and polymorphism is due to the partition of NaOH between the reaction medium and the non-oxidized regenerated cellulose chain. Non-oxidized regenerated cellulose can be swollen in concentrated NaOH, but not dissolved.

Once the non-oxidized regenerated cellulose is in the swell state (after NaOH immersion), further chemical reaction to form any kind of cellulose derivative can take place. The nature of the bound side chain will define the kind of cellulose derivative that can be synthesized. In carboxymethyl cellulose, an ionic carboxyl group is introduced at the end of the side chain as shown in FIG. 2.

Figure 2:
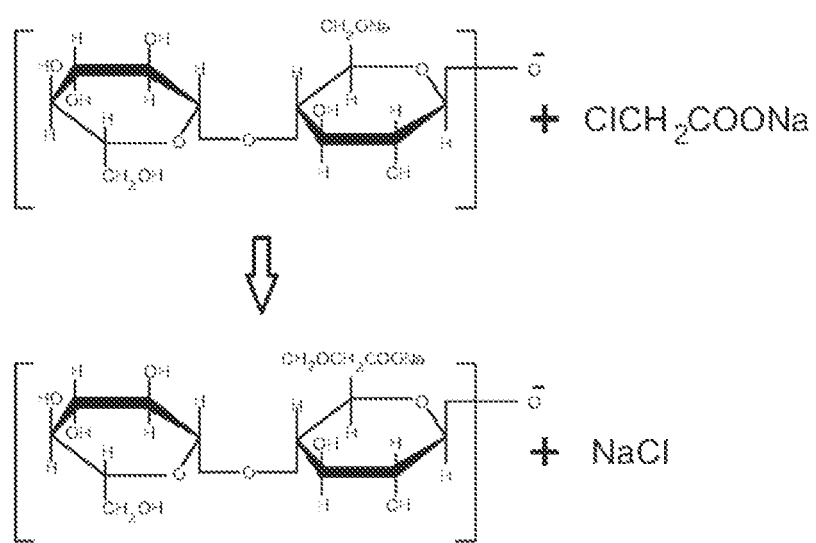
FIG. 2 is a reaction mechanism diagram of an etherification process performed on an alkali-cellulose of a carrier material, according to an embodiment.

FIG. 2 is a schematic molecular structure diagram illustrating reaction mechanism 200 of an etherification process performed on an alkali-cellulose of a carrier material, according to an embodiment. In this example, monochloroacetic acid mixed with NaOH in the presence of alkali-cellulose causes formation of a white sedimentation. This white sediment is sodium chloroacetate, which is re-dissolved and binds to the activated hydroxyl-cellulose to form carboxymethyl cellulose as shown in FIG. 2.

Carboxymethyl cellulose prepared by reacting alkali-cellulose with sodium monochloroacetic acid utilizes the "alkali consumption reaction" mechanism. The methylation proceeds as a nucleophilic substitution by the interaction of the oxonium sodium hydroxide complexes on accessible cellulose hydroxyls with methyl halide. Sodium hydroxide is consumed in this reaction, which means that the initial charge has to be so high that NaOH is present in sufficient supply to maintain an alkaline pH throughout etherification process.

Process Description

The manufacturing process comprises the following steps: an alkali treatment, preparation of an acid solution, a dissolution process, an etherification process, a washing and neutralization process, a drying process, and a sterilization process.

In some embodiments, the alkali treatment and the preparation of the acid solution can be completed simultaneously. In other embodiments, alkali treatment and the preparation of the acid solution can be completed in any order.

At the alkali treatment, a suitable amount of non-oxidized regenerated cellulose is introduced into the main vessel at room temperature, and a sodium hydroxide (NaOH) solution is added to the main vessel, with subsequent thorough impregnation of the non-oxidized regenerated cellulose, and stirring for between 3 to 5 hours at room temperature. In some embodiments, the sodium hydroxide solution used as the alkalization agent comprises: about 22.5 weight parts of about 48% to 51% aqueous sodium hydroxide solution, about 70.5 weight parts of absolute ethanol, and about 7.0 weight parts of soft water.

In one example, 1 kg of non-oxidized regenerated cellulose is introduced into the main vessel at room temperature, and a sodium hydroxide (NaOH) solution is added to the main vessel, with subsequent thorough impregnation of the non-oxidized regenerated cellulose, and stirring for about 3 hours at room temperature. In this example, the sodium hydroxide solution comprises: about 19 kg of ethanol, about 6.08 kg of a 48% aqueous sodium hydroxide solution, and about 1.9 kg of soft water, added in this order.

Simultaneously, an acid solution is prepared in the secondary vessel. The acid solution comprises: about 3.6 weight parts of soft water, about 53.6 weight parts of absolute ethanol, and about 42.8 weight parts of chloroacetic acid in the form of flake, with subsequent stirring for about 15 minutes at about 30° C., until the solution is completely homogeneous.

In one example, 0.38 kg of soft water are added to the secondary vessel, followed by about 5.7 kg of ethanol, and about 4.56 kg of chloroacetic acid flakes, with subsequent stirring for about 15 minutes at about 30° C.

At the beginning of the dissolution process, the sodium hydroxide solution for the alkali treatment is transferred to the secondary vessel containing the acid solution. A sedimentation salt is formed by the reaction of the alkali solution with the acid solution. At this stage, the sedimentation salt must be dissolved. To improve dissolution of the partial solids in the solution, heat is applied in a heating process. In various implementations, temperature ranges in the heating process should be kept from about 40° C. to about 60° C., with about 50° C. being preferred.

In the dissolution process, partial solid dissolution is achieved by mixing the solution including the sedimentation salt at about 50° C., which produces or obtains a solution for the etherification of the non-oxidized regenerated cellulose. The mixing time ranges from about 2 to about 7 hours, with about 4 hours being preferred. In some embodiments, a suitable mixing device is used for the mixing process, such as, for example mechanical double blade stirrer, or the like.

The dissolution of the sediment in the partial solid solution is implemented to obtain an improved hemostatic device.

By using a solution above the solubility threshold and by increasing the solution temperature, a saturated solution is created during the whole reaction time. In this way, during the etherification process the fabric is constantly immersed in the saturated solution thereby motivating the chemical potential of the reaction toward formation of covalent bonds on the cellulose backbone. Once the substitution occurs and the dissolved molecule is bound to another chain, the molecule is then dissolved into the available solvent medium to bind to a new chain. In this way, the concentration of the free dissolved chains remains constant during the whole reaction time.

The etherification process comprises: gradually transferring the solution obtained during the dissolution process to the main vessel to fully cover the non-oxidized regenerated cellulose for impregnation. The temperature range of the solution obtained during the dissolution process must be kept from about 40° C. to about 60° C. to avoid sediment formation.

In one embodiment, heat is applied in a heating process to the impregnated non-oxidized regenerated cellulose. In this embodiment, temperature ranges of the impregnated non-oxidized regenerated cellulose must be kept from about 40° C. to about 60° C., with about 50° C. being preferred. A mixing process is carried out to achieve complete impregnation of the non-oxidized regenerated cellulose during the etherification process. The mixing time ranges are from about 2 to about 24 hours, with about 12 hours being preferred. In some embodiments, a suitable mixing device is used for the mixing process, such as, for example a magnetic stirrer, or the like.

Subsequently, the remaining etherification solution is drained out of the main vessel containing the non-oxidized regenerated cellulose.

In some embodiments, the etherification process is part of the process of the substitution of the functional groups to produce sodium carboxymethyl cellulose. In other embodiments, the etherification process can produce other cellulose derivatives in the same mode of operation by using other monohalo-organic compound.

At the washing and neutralization process, the sodium carboxymethyl cellulose is washed and neutralized for pH control and stabilization.

In an example, the washing and neutralization process comprises: adding absolute ethanol to the main vessel until the sodium carboxymethyl cellulose is fully covered. About 50 mL amounts of hydrochloric acid are added to adjust pH of the solution until pH is in the range of about 4 to about 4.5. The sodium carboxymethyl cellulose is mixed with the ethanol and the hydrochloric acid for about 12 hours at about 25° C.; subsequently, the ethanol solution is drained out.

The drying process is carried out to fully dry the sodium carboxymethyl cellulose after the chemical treatment. In one embodiment, the drying process is performed using any suitable drying method/device, such as drum dryer, hot air dryer, or the like.

The sterilization process is carried out to sterilize the sodium carboxymethyl cellulose. In some embodiments, sterilization is performed using a suitable sterilization method/device, such as, for example gamma radiation, steam sterilization, peracetic acid liquid sterilization, ethylene oxide sterilization, hydrogen peroxide sterilization, among others. In some embodiments, the sterilization process is carried out before the drying process.

In one embodiment, the sterilization process is performed by radiating the carboxymethyl cellulose with gamma radiation. In this embodiment, the carboxymethyl cellulose is exposed to gamma radiation in a dose of from about 10 to about 40 kilograys.

The non-oxidized regenerated cellulose treated in this manner formed a sodium carboxymethyl cellulose with the target etherification degree (level of carboxymethyl group substitution) of about 0.88.

In other embodiments, improved hemostatic devices in carrier form of films and sponges can be produced by completely dissolving the prepared cellulose derivative using a dissolving agent, molding the dissolved cellulose derivative into the desired shape (e.g., for films as thin layers, for sponges with air bubbling), and then evaporating the dissolving agent. Suitable dissolving agents include suitable organic solvents, water or a mixture of suitable organic solvents.

The sodium carboxymethyl cellulose obtainable by this process dissolves in a bioabsorbable, biodegradable, biocompatible manner or nature, thereby allowing it to be used as a hemostatic device safely, both internally and externally. These hemostatic devices have a unique level of adherence and gel stability.

The present disclosure enables manufacture of biocompatible, biodegradable, bioabsorbable, water soluble carboxymethyl cellulose used for an improved hemostatic device having high levels of absorption, and a unique level of adherence and gel stability, thereby allowing high efficient bleeding control for non-compressional and/or non-tourniquetable injuries, among other things.

While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. A hemostatic device, comprising:
non-oxidized, non-regenerated sodium carboxymethyl cellulose (Na-CMC) having a level of carboxymethyl group substitution of about 0.88; wherein:
the non-oxidized, non-regenerated Na-CMC forms a hemodynamic gel when it contacts blood, wherein the Na-CMC is formed by a process comprising:
an alkali treatment comprising exposing non-oxidized, non-regenerated cellulose to a sodium hydroxide solution at a first temperature;
forming an acid solution comprising chloroacetic acid;
forming a saturated solution comprising the alkali-treated non-oxidized, non-regenerated cellulose, the sodium hydroxide solution, and the acid solution, wherein the saturated solution comprises sedimentary salt, and has a water to ethanol ratio up to about 22%;
dissolving the sedimentary salt by mixing the saturated solution at a second temperature of about 40° C. to about 60° C. for about four hours to about seven hours to form a solution for etherification, wherein the second temperature is higher than the first temperature; and
forming the non-oxidized, non-regenerated Na-CMC in the saturated solution for about two to about twenty four hours at a temperature of about 40° C. to about 60° C., the saturated solution having a water to ethanol ratio up to about 22%.

2. The hemostatic device of claim 1, wherein the first temperature is room temperature and the second temperature is from about 40° C. to about 60° C.

3. The hemostatic device of claim 2, wherein the saturated solution is mixed at a temperature of about 50° C.

4. The hemostatic device of claim 1, wherein the saturated solution is mixed for about four hours.

* * * * *